United States Patent [19]
Kelly et al.

[11] Patent Number: 5,542,435
[45] Date of Patent: Aug. 6, 1996

[54] DISPOSABLE SURGICAL SHIELD

[75] Inventors: Kenneth W. Kelly; Anthony W. Malone, both of, Portsmouth; Jeffrey S. Humble, Lucasville, all of Ohio

[73] Assignee: Teays Quality Molding, Inc., Lucasville, Ohio

[21] Appl. No.: 395,148

[22] Filed: Feb. 27, 1995

[51] Int. Cl.⁶ ............................ A61F 5/37; A61B 17/32
[52] U.S. Cl. ............................ 128/846; 606/170
[58] Field of Search ........................ 128/845, 846, 128/849–856, 897; 606/119, 120, 170

[56] References Cited

U.S. PATENT DOCUMENTS 1,600,225 9/1926 Halpern .
3,010,206 11/1961 Curry ................................. 30/131
3,807,406 4/1974 Rafferty et al. ................... 128/318
4,949,734 8/1990 Bernstein .......................... 128/897
5,178,624 1/1993 Kyun ................................ 606/120
5,190,556 3/1993 Hessel .............................. 606/120
5,385,570 1/1995 Chin ................................ 606/170
5,395,386 3/1995 Slater .............................. 606/170

*Primary Examiner*—Michael A. Brown
*Attorney, Agent, or Firm*—John L. Gray

[57] ABSTRACT

The invention is a disposable shield for use on surgical scissors to protect surgical personnel from spurting blood when the umbilical cord is cut. It has a generally triangular shield portion and an elongated member with a channel in it so the shield can be easily attached to the arm of the surgical scissors.

11 Claims, 1 Drawing Sheet

DISPOSABLE SURGICAL SHIELD

BACKGROUND OF THE INVENTION

This invention relates to surgical shields and more particularly to a disposable surgical shield to be attached to surgical scissors.

During the delivery of babies, the umbilical cord is cut shortly after birth. The umbilical cord transfers oxygen and nutrients from the mother to the baby, and waste products from the baby to the mother. Prior to cutting the cord, clamps are placed on the cord to stop the flow of blood. The area between the two clamps is under pressure, and when the umbilical cord is cut, blood spurts out. Since blood can carry diseases, such as AIDS, it is desirable to prevent the blood from spraying as much as possible.

Therefore, it is an object of this invention to provide a surgical shield to protect surgical personnel from spraying blood when cutting the umbilical cord.

It is a further object to provide a disposable shield which can be easily attached to and removed from surgical scissors.

It is still another object to provide a disposable shield which allows surgical personnel to see the area to be cut while protecting them from spraying blood.

These, together with other objects and advantages of the inventions will become more readily apparent to those skilled in the art when the following general statements and descriptions are read in the light of the appended drawings.

SUMMARY OF THE INVENTION

The invention is a disposable shield adapted to be releasably attached to the arm of surgical scissors. The shield comprises means for releasably attaching the disposable shield to the surgical scissors and a shield portion extending over the cutting portion of the surgical scissor.

The shield portion is generally triangular in shape, and it can have sides which may be tapered. The edges and corners of the disposable shield are rounded to prevent injury to the mother or baby.

The shield portion is preferably attached to the surgical scissors with an elongated member which has a channel extending through it to receive the arm of the surgical scissor. The channel preferably has wings extending inwardly on each side. This allows the shield to be secured on the arm of the surgical scissors.

DETAILED DESCRIPTION OF THE INVENTION

Figure 1:
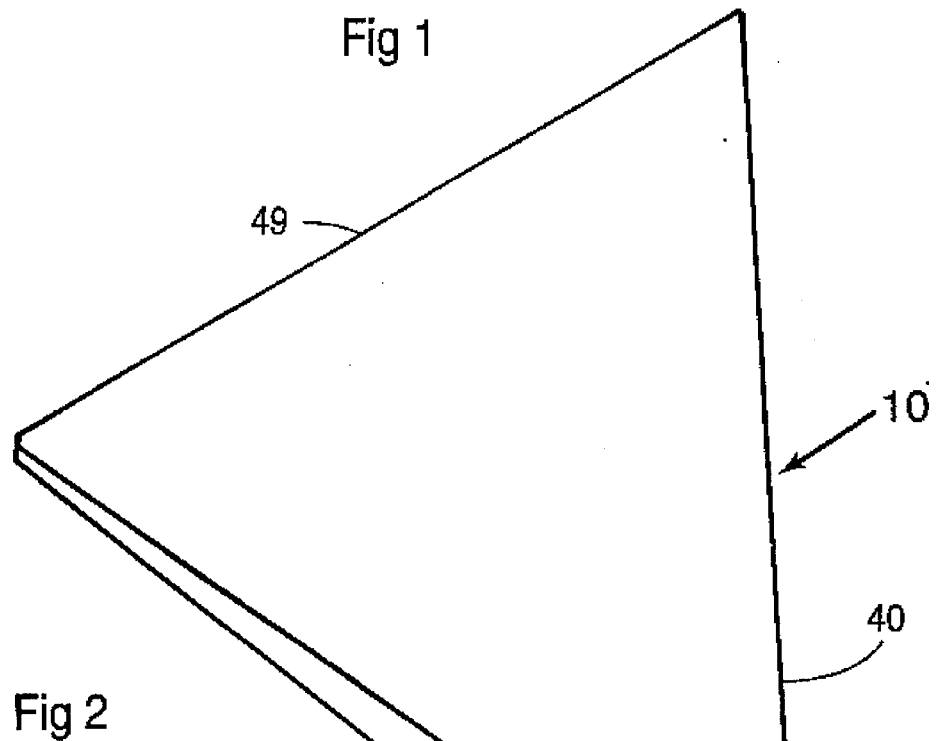
FIG. 1 is a perspective view of the disposable shield.
Figure 2:
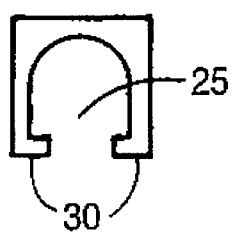
FIG. 2 is a section view of the elongated member of the disposable shield.

The preferred embodiment of the disposable shield 10 of the present invention is shown in FIG. 1. The disposable shield 10 has two parts, an elongated member 20 and a shield portion 40. The elongated member 20 has a channel 25. The upper portion of the channel 25 is curved to match the shape of the arm of the surgical scissors. On the bottom of the channel 25 are wings 30—30 which extend inwardly from each side. FIG. 2 shows a section of the elongated member 20 including the channel 25 and wings 30—30. The arm of the surgical scissors fits into channel 25. The wings 30—30 allow the elongated member 20 to lock onto the arm of the surgical scissors and prevent the disposable shield from rotating.

The shield portion 40 extends over the cutting portion of the surgical scissors. It is generally triangular in shape. The shield portion preferably includes side portions 45. The side portions 45 are substantially perpendicular to the shield portion 40 and may be tapered from the base 47 of the shield portion to the end opposite the base 49. The edges and corners of the disposable shield are preferably rounded to prevent injury to either the baby or the mother.

The shield portion is preferably at a 45° angle with respect to the elongated member. However, any angle would work.

Figure 3:
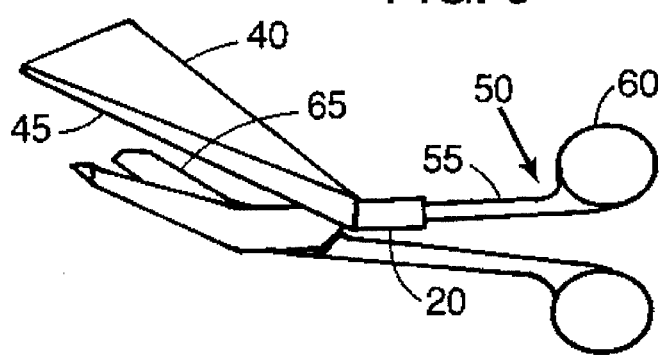
FIG. 3 is a perspective view of the disposable shield attached to a pair of surgical scissors.

The disposable shield 10 is shown attached to the surgical scissors 50 in FIG. 3. The elongated member 20 is placed over an arm 55 of the surgical scissors 50. The arm 55 increases in width going from the thumb loop 60 toward the cutting portion 65. The elongated member 20 is pushed along the arm 55 toward the cutting portion 65 until it will go no farther. The wings 30—30 on the channel 25 of the elongated member 20 lock the arm in place and prevent the shield from rotating.

The shield portion 40 of the disposable shield 10 extends over the cutting portion 65 of the surgical scissors 50. The disposable shield 10 is essentially clear, so that the surgical personnel can easily see the area to be cut. When the cut is made, the shield portion 40 protects the surgical personnel from the blood spurting from the umbilical cord. After the umbilical cord has been cut, the disposable shield 10 is removed from the surgical scissors 50 by sliding the disposable shield 10 up the arm 55 toward the thumb loop 60 of the surgical scissors 50 and lifting it off. The disposable shield 10 can then be disposed of properly.

The disposable shield may be made from any essentially clear polymeric material. It is preferably made from polycarbonate, but it may be made from other essentially clear polymers such as polystyrene, K-resin, or acrylic polymers, such as polymethyl methacrylate.

Other means of attaching the shield portion 40 to the arm of the surgical scissors 55 may be used. Hooks, clamps, and hook and loop closures are examples of means of attaching that could be used.

While a preferred form of the invention has been shown in the drawings and described, since variations in the preferred form will be apparent to those skilled in the art, the invention should not be construed as limited to the specific form shown and described, but instead is as set forth in the following claims.

What is claimed is:

1. A disposable shield adapted to be releasably attached to an arm of a surgical scissor provided with two blades and comprising:

means for releasably attaching the disposable shield only to an arm of said surgical scissor;

a shield portion extending over said two blades of said surgical scissor when said blades are performing a cutting operation; and said shield portion being substantially triangular in shape and of a size to cover said blades from an extended to a closed position, whereby the user of said scissors is shielded from any fluids released from the subject matter being cut by said blades.

2. The disposable shield of claim 1 further comprising a side portion connected to the shield portion.

3. The disposable shield of claim 2 wherein the side portion is substantially perpendicular to the shield portion.

4. The disposable shield of claim 2 wherein the side portion is tapered from the base to the end opposite the base.

5. The disposable shield of claim 1 wherein the means for releasably attaching has a channel extending therethrough to receive the arm of the surgical scissor.

6. The disposable shield of claim 5 wherein the channel has a wing extending inwardly from each side of the channel, whereby the wings secure the disposable shield on the arm of the surgical scissor.

7. The disposable shield of claim 1 wherein the edges and corners are rounded to prevent injury.

8. The disposable shield of claim 1 wherein the disposable shield is made from an essentially clear polymeric material.

9. The disposable shield of claim 8 wherein the essentially clear polymeric material is selected from the group consisting of polystyrene, polycarbonate, K-resin, and acrylic polymers.

10. The disposable shield of claim 9 wherein the essentially clear polymeric material is polycarbonate.

11. The disposable shield of claim 10 wherein the essentially clear polymeric material is polystyrene.

* * * * *